(12) United States Patent
Chang et al.

(10) Patent No.: US 10,500,148 B2
(45) Date of Patent: Dec. 10, 2019

(54) PHYTONCIDE MOISTURIZING LIQUID COMPOSITION, HYDROGEN-GENERATING SKIN CARE SPRAY DEVICE COMPRISING SAME, AND METHOD FOR PREPARING SAME

(71) Applicant: QWELL CO., LTD., Gunpo-si, Gyeonggi-do (KR)

(72) Inventors: Je-Won Chang, Namyangju-si (KR); Hyun-Jin Chang, Namyangju-si (KR)

(73) Assignee: QWELL CO., LTD., Gunpo-si (KR)

( * ) Notice: Subject to any disclaimer, the term of this patent is extended or adjusted under 35 U.S.C. 154(b) by 0 days.

(21) Appl. No.: 15/559,043

(22) PCT Filed: Mar. 8, 2016

(86) PCT No.: PCT/KR2016/002280
§ 371 (c)(1),
(2) Date: Sep. 16, 2017

(87) PCT Pub. No.: WO2016/148420
PCT Pub. Date: Sep. 22, 2016

(65) Prior Publication Data
US 2018/0092824 A1 Apr. 5, 2018

(30) Foreign Application Priority Data
Mar. 16, 2015 (KR) .................. 10-2015-0035817

(51) Int. Cl.
*A61K 8/73* (2006.01)
*A61Q 19/00* (2006.01)
(Continued)

(52) U.S. Cl.
CPC .............. *A61K 8/736* (2013.01); *A45D 34/04* (2013.01); *A61K 8/88* (2013.01); *A61K 8/96* (2013.01);
(Continued)

(58) Field of Classification Search
CPC .. A45D 34/04; A45D 2200/058; A61Q 19/00; B65D 83/0055; B65D 83/42;
(Continued)

(56) References Cited

U.S. PATENT DOCUMENTS

2009/0236363 A1* 9/2009 Haley .................... B32B 15/08
222/95
2010/0264165 A1* 10/2010 Hansen .................. B32B 15/08
222/95
2016/0249725 A1* 9/2016 Hasegawa .............. A45D 34/00
222/96

FOREIGN PATENT DOCUMENTS

JP 2004-041949 A 2/2004
KR 20-0421890 Y1 7/2006
(Continued)

OTHER PUBLICATIONS

Nakao et al., "Effectiveness of Hydrogen Rich Water on Antioxidant Status of Subjects with Potential Metabolic Syndrome-An Open Label Pilot Study", Journal of Clinical Biochemistry and Nutrition, vol. 46, Issue 2, Mar. 2010, pp. 140-149.
(Continued)

*Primary Examiner* — Darren W Gorman
(74) *Attorney, Agent, or Firm* — Maschoff Brennan

(57) ABSTRACT

Disclosed are a phytoncide moisturizing liquid composition, a hydrogen-generating skin care spray device including the same, and a method for preparing the same, wherein a phytoncide moisturizing liquid composition, which contains, on the basis of the total weight of the composition, about 95-98 wt % of water, about 1-3 wt % of a phytoncide undiluted liquid, about 0.05-0.5 wt % of gamma poly L glutamic acid, about 0.05-0.5 wt % of chitosan, and about 0.1-2 wt % of an emulsifier, is mixed with hydrogen generated by a hydrogen generator, thereby maximizing, at one time, the effect of the phytoncide moisturizing liquid
(Continued)

composition, which is capable of suppressing the increase in collagenase in the skin due to ultraviolet radiation, and the effect of the hydrogen, which suppresses melanin synthesis by ultraviolet radiation and makes active oxygen generated due to the ultraviolet radiation harmless to the human body.

5 Claims, 4 Drawing Sheets

(51) Int. Cl.
*A45D 34/04* (2006.01)
*A61K 8/88* (2006.01)
*A61K 8/96* (2006.01)
*A61K 8/9761* (2017.01)

(52) U.S. Cl.
CPC ............ *A61K 8/9761* (2017.08); *A61Q 19/00* (2013.01); *A45D 2200/058* (2013.01); *A61K 2800/87* (2013.01)

(58) Field of Classification Search
CPC ...... B65D 83/62; B65D 83/75; B65D 83/752; B65D 83/753; B65D 83/754; B05B 7/24; B05B 7/241; B05B 7/2416
See application file for complete search history.

(56) References Cited

FOREIGN PATENT DOCUMENTS

| | | | |
|---|---|---|---|
| KR | 10-2010-0101328 | A | 9/2010 |
| KR | 10-2013-0033228 | A | 4/2013 |
| KR | 10-1367703 | B1 | 3/2014 |
| KR | 10-2014-0049684 | A | 4/2014 |
| KR | 10-1439385 | B1 | 9/2014 |
| WO | 2010/104301 | A2 | 9/2010 |

OTHER PUBLICATIONS

Krause et al., "Sunscreens: are they beneficial for health? An overview of endocrine disrupting properties of UV-filters", International Journal of Andrology, Jun. 2012, vol. 35, No. 3, pp. 424-436.

Yu, et al., "Associations between Serum 25-hydroxyvitamin D and Consumption Frequencies of Vitamin D Rich Foods in Korean Adults and Older Adults," Korean Journal of Community Nutrition, vol. 19, No. 2, pp. 122-132.

Fujimori et al., "Inhibitory Effects of Phytoncide Solution on Melanin Biosynthesis", Bioscience, Biotechnology, and Biochemistry, vol. 74, Issue 5, 2010, pp. 918-922.

Fujimori et al., "Protecting Effect of Phytoncide Solution, on Normal Human Dermal Fibroblasts against Reactive Oxygen Species", Journal of Oleo Science, vol. 58, Issue 8, 2009, pp. 429-436.

* cited by examiner

PHYTONCIDE MOISTURIZING LIQUID COMPOSITION, HYDROGEN-GENERATING SKIN CARE SPRAY DEVICE COMPRISING SAME, AND METHOD FOR PREPARING SAME

TECHNICAL FIELD

The present invention relates to a phytoncide moisturizing liquid composition, a hydrogen-generating spray device for skin care including the same, and a method of manufacturing the same. More particularly, the present invention relates to a phytoncide moisturizing liquid composition, a spray device for skin care including the same, and a method of manufacturing the same so as to address problems, such as coarse particles causing displeasure and running of a sprayed liquid on the face even when the liquid is sprayed in a small amount, upon use of a conventional pump-type nozzle, and to maximize the effects of hydrogen and phytoncide.

BACKGROUND ART

When the skin is exposed to ultraviolet light, UV photons (290 to 315 nm) pass through the skin. UV photons are known to photodegrade 7-dehydrocholesterol in cells and convert the photodegraded 7-dehydrocholesterol into previtamin D3, as a precursor of vitamin D, thereby promoting the biosynthesis of vitamin D in the body (Fed Proc. 1987; 46: 1876-1882).

Vitamin D is involved in cardiovascular diseases, bone formation, autoimmune disease inhibition, and the like. (December 2010, Hyun Cho, Medicine Department of Soonchunhyang University, RELATIONSHIP BETWEEN VITAMIN D AND VARIOUS DISEASES). It was reported that vitamin D deficiency increases the occurrence frequencies of cancers such as breast cancer and colorectal cancer (February 2012, Jihyun Lee, Konkuk University, ANTICANCER EFFECT OF VITAMIN D3 ON HUMAN MELANOMA CELLS).

In accordance with research on Korean adult men and women, it was reported that serum concentrations of vitamin D in about 50% of adult men and women aged 19 to 69 years did not exceed an appropriate level, 20 ng/ml, (Korean Journal of Community Nutrition, 2014; 19: 122-132).

Ultraviolet rays play an important role in stimulating biosynthesis of vitamin D in the skin, but induce melanin pigmentation, causing darkening of the skin (Biotechnol. Biochem., 74(5), 918-922, 2010). In addition, ultraviolet rays are known to promote skin aging by increasing the expression of collagenase and inhibiting collagen synthesis (J. Oleo Sci. 58(8)429-436 (2009).

When the skin is exposed to ultraviolet rays, the amount of an enzyme called matrix metalloproteinase-1 (MMP-1) is increased. Since this enzyme rapidly decomposes collagen, the skin loses elasticity and wrinkles.

Ultraviolet sunscreens are generally used for cosmetic purposes so as to suppress or avoid the side effects of ultraviolet rays. However, such an ultraviolet sunscreen includes benzophenone-3 (BP-3), 3-benzylidene camphor (3-BC), 3-(4-methyl-benzylidene) camphor (4-MBC), 2-ethylhexyl 4-methoxy cinnamate (OMC), homosalate (HMS), 22-ethylhexyl 4-dimethylaminobenzoate (OD-PABA), 4-aminobenzoic acid (PABA), and the like which are reported to be carcinogenic or affect the reproductive endocrine and thyroid endocrine systems of the body (Int J Androl. 2012; 35: 424-436).

Meanwhile, reactive oxygen species (ROS) in the body are naturally produced by normal metabolism of oxygen, but are also generated by external factors such as X-rays, ozone, smoke, air pollution, electromagnetic waves, residual pesticides, and stress.

These ROS, which contain oxygen ions and peroxides and are highly reactive substances oxidizing other substances in the body due to unpaired electrons (non-covalent electron pairs), may destroy normal cells.

Interestingly, melanin generation due to ultraviolet rays is caused by excessive pigmentation of the skin, and skin aging is known to be mediated by ROS.

Melanin is produced through a series of oxidation reactions of the amino acid tyrosine. Tyrosinase is known to play an important role in melanin generation. It was reported that, when the activity of the enzyme is regulated, excessive sedimentation is inhibited (J. Oleo, Sci. 58 (8), 429-436, 2009).

Meanwhile, superoxide dismutase, as the most potent antioxidant enzyme, converts superoxide anion radicals ($O^{2-}$) generated by ultraviolet rays into less harmful hydrogen peroxide ($H_2O_2$) which is again decomposed into water and oxygen ($2H2O2 \rightarrow 2H2O+O2$) by GPX and a catalase to be used for metabolism in the human body, thereby eliminating damages due to ROS.

In addition, superoxide dismutase (SOD) was investigated to suppress the production of alpha-melanocyte stimulating hormone and the increase of melanin production due to UV-B exposure.

Recent studies have reported that the antioxidative effects of hydrogen are caused by activity increase of superoxide dismutase (SOD) contained in blood (J. Clin. Biochem. Nutr. 46, 140-149, 2010, 3). Accordingly, hydrogen is considered to sufficiently complement the aforementioned superoxide dismutase functions.

Recently, many cases of utilizing hydrogen, which is generated through a simple chemical reaction (Mg+ $2H_2O \rightarrow Mg(OH)_2+H_2$), for skin care and the like are reported in Japan and other countries. Hydrogen has been reported to have antioxidant effect of selectively reducing cytotoxicity of ROS that damage cells.

In addition, through animal experiments and human clinical trials in which drinking water including hydrogen (hydrogen rich water) was used, it was known that hydrogen therapy, which increases hydrogen supply, induces decrease in cytotoxicity and decrease in cytotoxicity due to carbon monoxide.

Meanwhile, phytoncides, as natural products, are volatile substances released from land plants and are known to inhibit the enzymatic activity of tyrosinase, as an important enzyme for the production of melanin. In addition, phytoncides were reported to inhibit cellular damage due to UV-A and UV-B, active oxygen ($H_2O_2$) and tert-butyl-hydroperoxide (t-BHP), and promote the generation of collagen in skin cells.

In addition, it was reported that, when the skin is exposed to ultraviolet rays, an enzyme called tyrosinase produces melanin, which darkens the skin, but phytoncides regulate the production of melanin by inhibiting the activity of tyrosinase.

It was reported that, when cellular damage due to oxidative stress was examined after phytoncides were applied to the normal skin and then the skin was irradiated with UV-B and UV-A, phytoncides extracted from cypress reduced a generation amount of an enzyme MMP-1 decomposing collagen in the normal skin by 83% or more when the skin is irradiated with UVA (J. Oleo Sci. 58 (8) 429-436, 2009).

In addition, phytoncides have been reported to have physiological effects, such as rapid anti-aging effect, alleviation of allergies, various cirrhosis types, Parkinson's disease, and the like, and activation of natural killer (NK) cells as immune cells.

Meanwhile, when phytoncides are directly applied to the skin, anti-wrinkle and antioxidant effects are exhibited. In addition, when phytoncides are sprayed along with hydrogen on the skin, the phytoncides and hydrogen are quickly absorbed into the skin.

As products on which the aforementioned points were reflected, spray-type products wherein phytoncides extracted from cypress were diluted to a concentration of 3% or less were manufactured. These spray-type products are generally composed of 97% of water and 3% of phytoncides. In the case in which only phytoncides are used, a general plastic container is used. In addition, since hydrogen is stored in a general plastic container also in the cases of products using hydrogen, there are few methods of preventing hydrogen leakage through pores of a wall of the plastic container.

Accordingly, the present inventors attempted to develop a phytoncide moisturizing liquid composition, a hydrogen-generating spray device for skin care including the same, and a method of manufacturing the same so as to allow effective use of the phytoncide moisturizing liquid composition without waste of hydrogen, and effective skin care due to effects, such as vitamin D synthesis, inhibition of melanin synthesis, inhibition of collagen decomposition, collagen synthesis, and decomposition of active oxygen, using synergistic effects of hydrogen and the phytoncide moisturizing liquid composition.

RELATED ART DOCUMENTS

Patent Documents (Patent Document 1) Korean Patent No. 10-1439385 (Registered on Sep. 2, 2014)
(Patent Document 2) Korean Patent No. 10-1367703 (Registered on Feb. 20, 2014)

DISCLOSURE

Technical Problem

Therefore, the present invention has been made in view of the above problems, and it is one object of the present invention to provide a phytoncide moisturizing liquid composition for protecting cells from ultraviolet rays and active oxygen and allowing effective collagen generation.

It is another object of the present invention to provide a phytoncide moisturizing liquid composition, a skin care spray device for hydrogen generation to suppress melanin synthesis due to ultraviolet rays and to allow use of a mixture of the phytoncide moisturizing liquid composition with hydrogen capable of removing active oxygen, and a method of manufacturing the same.

Technical Solution

In accordance with one aspect of the present invention, provided is a phytoncide moisturizing liquid composition, including: about 95 to 98% by weight of water; about 1 to 3% by weight of an undiluted phytoncide solution; about 0.05 to 0.5% by weight of gamma-poly L-glutamic acid; about 0.05 to 0.5% by weight of chitosan; and about 0.1 to 2% by weight of an emulsifier, based on a total weight of the phytoncide moisturizing liquid composition.

Here, the phytoncide moisturizing liquid composition preferably, further includes about 0.1 to 2% by weight of a botanical extract, and the botanical extract is preferably an aloe extract, a citrus oil, or the like.

In accordance with another aspect of the present invention, provided is a skin care spray device for hydrogen generation, including: a hydrogen-generating ceramic filter including a porous ceramic container, one opened end of which is sealed with a ceramic cap, so as to prevent external leakage of magnesium fragments; an aluminum pouch containing the hydrogen-generating ceramic filter and a phytoncide moisturizing liquid composition and provided with a check valve for preventing the phytoncide moisturizing liquid composition from running back from an upper part of the aluminum pouch; a cylindrical aluminum can, an open upper part of which is coupled with an upper part of the aluminum pouch; a nozzle for spraying the phytoncide moisturizing liquid composition filled in the aluminum pouch, the nozzle being mounted on an upper part of the aluminum can; and the like.

Here, the cylindrical aluminum can sealed preferably includes air having a predetermined pressure therein and the like, wherein the pressure of the air is preferably about 6 to 9 bar.

In addition, the phytoncide moisturizing liquid composition preferably includes about 95 to 98% by weight of water, about 1 to 3% by weight of an undiluted phytoncide solution, about 0.05 to 0.5% by weight of gamma-poly L-glutamic acid, about 0.05 to 0.5% by weight of chitosan, about 0.1 to 2% by weight of an emulsifier, and the like based on a total weight of the phytoncide moisturizing liquid composition.

Here, the phytoncide moisturizing liquid composition preferably, further includes about 0.1 to 2% by weight of a botanical extract, and the botanical extract is preferably an aloe extract, a citrus oil, or the like.

In accordance with yet another aspect of the present invention, provided is a method of manufacturing a skin care spray device for hydrogen generation, the method including: a step of manufacturing a hydrogen-generating ceramic filter by inserting magnesium fragments into a porous ceramic container that has been subjected to plastic working, and sealing a ceramic cap; a step of cutting a lower part of a prepared aluminum pouch and then inserting the manufactured hydrogen-generating ceramic filter into the aluminum pouch, followed by sealing the cut portion of the aluminum pouch; a step of coupling an upper part of the aluminum pouch including the hydrogen-generating ceramic filter therein with an upper part of a cylindrical aluminum can and sealing the aluminum can such that air in the aluminum can does not escape to the outside; a step of mixing water, an undiluted phytoncide solution, gamma-poly L-glutamic acid, chitosan, an emulsifier, and the like by means of a homomixer at about 15 to 25° C. for about 1 to 3 hours, and then preparing the phytoncide moisturizing liquid composition having an average particle diameter of greater than 0 nm and about 20 nm or less by means of a high-pressure nano homogenizer; a step of filling the aluminum pouch with the prepared phytoncide moisturizing liquid composition by forcibly injecting the prepared phytoncide moisturizing liquid composition into the aluminum pouch via the hole that includes a nozzle, which is located at an upper end of the aluminum can, mounted thereon and passes through the upper part of the aluminum pouch; a step of mounting the nozzle on an upper part of the aluminum can so as to spray the phytoncide moisturizing liquid composition filling the aluminum pouch into the atmosphere; and the like.

Here, the cylindrical aluminum can sealed preferably includes air having a predetermined pressure therein and the like, wherein the pressure of the air is preferably about 6 to 9 bar.

In addition, the phytoncide moisturizing liquid composition preferably includes about 95 to 98% by weight of water, about 1 to 3% by weight of an undiluted phytoncide solution, about 0.05 to 0.5% by weight of gamma-poly L-glutamic acid, about 0.05 to 0.5% by weight of chitosan, about 0.1 to 2% by weight of an emulsifier, and the like based on a total weight of the phytoncide moisturizing liquid composition.

Here, the phytoncide moisturizing liquid composition (120) preferably, further includes about 0.1 to 2% by weight of a botanical extract, and the botanical extract is preferably an aloe extract, a citrus oil, or the like.

Advantageous Effects

As apparent from the fore-going, the present invention having the aforementioned configuration provides a phytoncide moisturizing liquid composition mixed with hydrogen generated by a hydrogen generator, thereby suppressing increase of a collagenase in the skin caused by ultraviolet rays and simultaneously maximizing the effect of suppressing melanin synthesis by ultraviolet rays and the effect of hydrogen capable of making active oxygen generated by the melanin synthesis harmless to the human body, and allowing efficient use of the phytoncide moisturizing liquid composition saturated with the hydrogen without waste of the hydrogen by storing the generated hydrogen an aluminum pouch, from which the hydrogen does not leak.

In addition, the present invention may simultaneously satisfy convenience and functionality by facilitating portability and allowing convenient and effective skin moisturization and skin maintenance care.

BEST MODE

Figure 1:
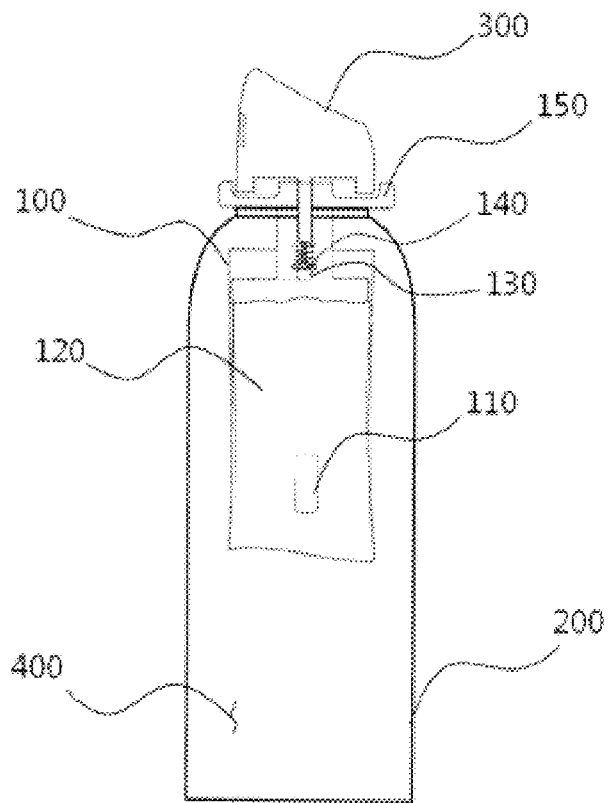
FIG. 1 illustrates an internal assembly diagram of a skin care spray device for hydrogen generation containing a phytoncide moisturizing liquid composition according to the present invention.
Figure 2:
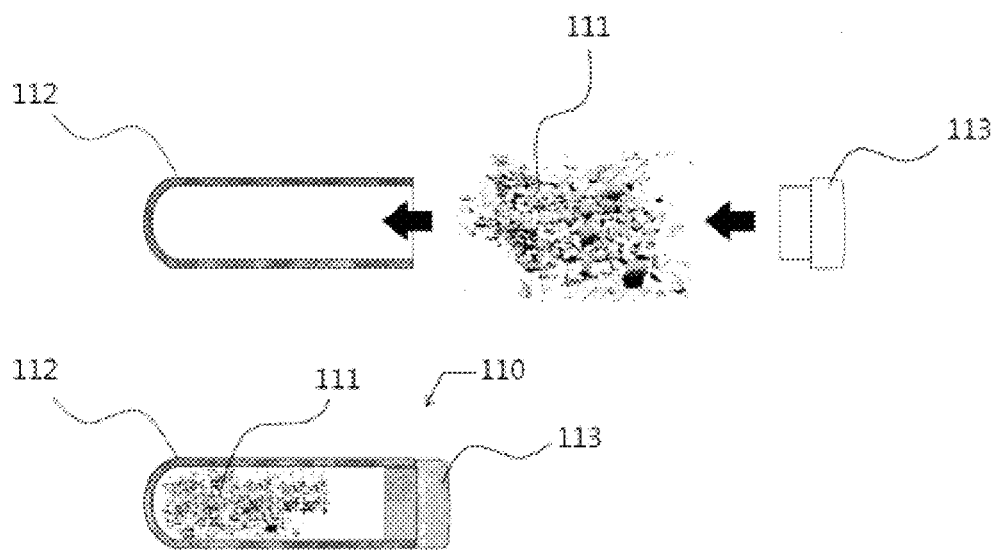
FIG. 2 illustrates sectional views of a hydrogen-generating ceramic filter.
Figure 3:
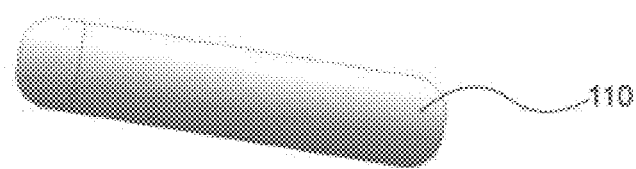
FIG. 3 illustrates a perspective view of a hydrogen-generating ceramic filter.
Figure 4:
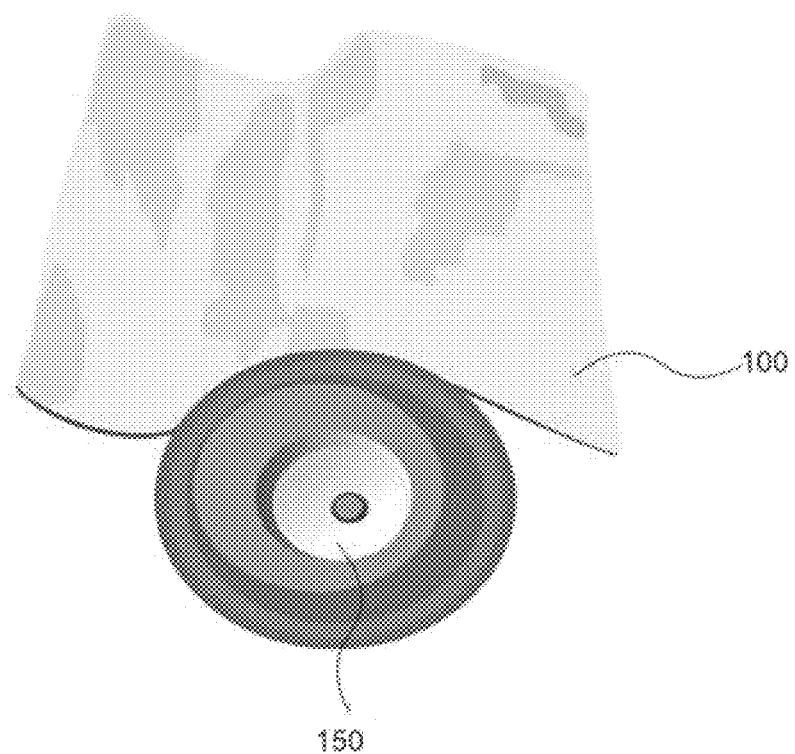
FIG. 4 illustrates a perspective view of an aluminum pouch.
Figure 5:
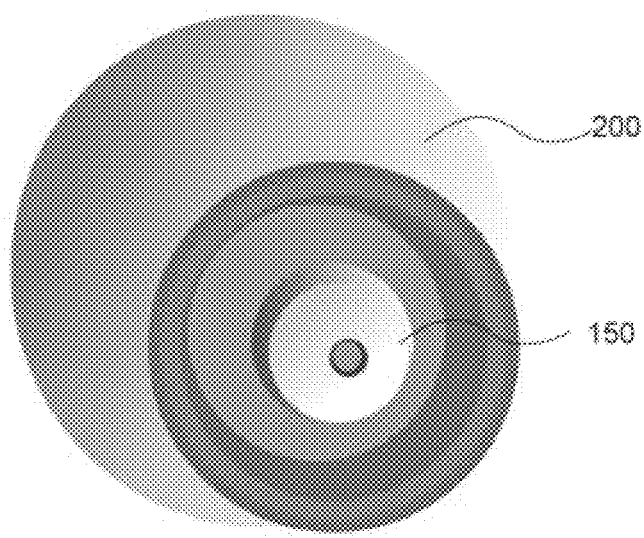
FIG. 5 illustrates an upper end of an aluminum pouch and an upper end of a can coupled thereto.
Figure 6:
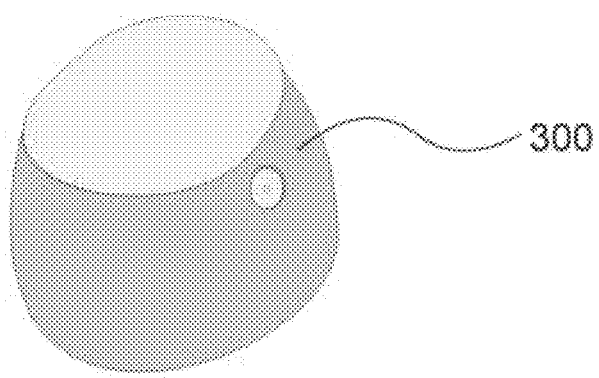
FIG. 6 illustrates a perspective view of a nozzle.
Figure 7:
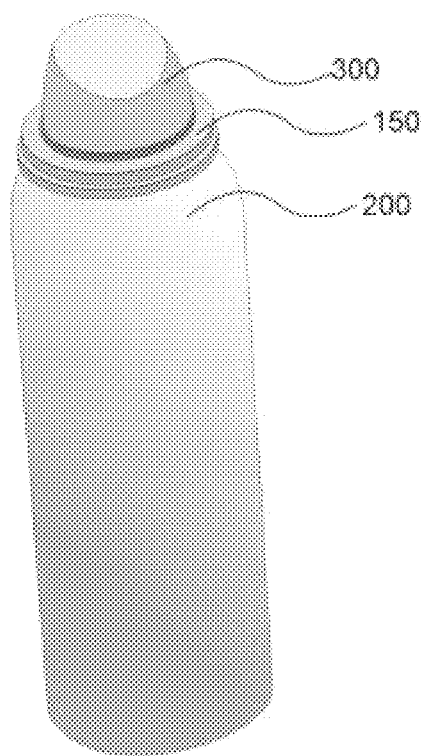
FIG. 7 illustrates a perspective view of a skin care spray device for hydrogen generation.

The meaning of the terms used in the specification and the appended claims should not be construed as being confined to common or dictionary meanings, but should be construed as concepts not departing from the technical spirit and scope of the present invention on the basis that the inventors can properly define the concepts of terms so as to explain their invention in the best way.

Hereinafter, the present invention is described in detail. The present invention relates to a phytoncide moisturizing liquid composition, a hydrogen-generating spray device for skin care including the same, and a method of manufacturing the same. In an aspect, the present invention relates to a phytoncide moisturizing liquid composition.

More particularly, the phytoncide moisturizing liquid composition according to the present invention includes water, an undiluted phytoncide solution, gamma-poly L-glutamic acid, chitosan, an emulsifier, and the like, as main ingredients. Here, the water is preferably ultrapure water.

Preferably, the amount of the water is about 95 to 98% by weight, the amount of phytoncide is about 1 to 3% by weight, the amount of gamma-poly L-glutamic acid is about 0.05 to 0.5% by weight, the amount of chitosan is about 0.05 to 0.5% by weight, and the amount of an emulsifier is about 0.1 to 0.2% by weight based on a total weight of the phytoncide moisturizing liquid composition. More preferably, the amount of the water is about 97.65% by weight, the amount of phytoncide is about 2% by weight, the amount of gamma-poly L-glutamic acid is about 0.1% by weight, the amount of chitosan is 0.1% by weight, and the amount of an emulsifier is about 0.15% by weight based on a total weight of the phytoncide moisturizing liquid composition.

In addition, the phytoncide moisturizing liquid composition according to the present invention may selectively, further include a botanical extract. Here, the content of the botanical extract is preferably about 0.1 to 2% by weight, and the botanical extract is preferably an aloe extract or a citrus oil.

In a more particular embodiment, the phytoncide moisturizing liquid composition according to the present invention preferably includes about 97.65% by weight of water, about 2% by weight of an undiluted phytoncide solution, about 0.1% by weight of gamma-poly L-glutamic acid, about 0.1% by weight of chitosan, about 0.15% by weight of an emulsifier, and the like based on a total weight of the composition.

In another embodiment, the phytoncide moisturizing liquid composition according to the present invention preferably includes about 96.65% by weight of water, about % by weight of an undiluted phytoncide solution, about 0.1% by weight of gamma-poly L-glutamic acid, about 0.1% by weight of chitosan, about 0.15% by weight of an emulsifier, about 1% by weight of an aloe extract, and the like based on a total weight of the composition.

In another embodiment, the phytoncide moisturizing liquid composition according to the present invention preferably includes 96.8% by weight of water, 1.5% by weight of an undiluted phytoncide solution, 0.1% by weight of gamma-poly L-glutamic acid, 0.1% by weight of chitosan, 1% by weight of an emulsifier, 0.5% by weight of a citrus oil, and the like based on a total weight of the composition.

Here, the undiluted phytoncide solution, as a phytoncide stock solution extracted from *chamaecyparis obtusa* trees, is preferably an oil from *chamaecyparis obtusa* trees afforested in or native to the southern provinces of Korea. Oil extracted from leaves of abandoned tress when thinning the forest may be used. In addition, a mixture of a domestic oil, which is extracted from domestic pine leaves, and a Japanese oil, which is extracted from xylem of *chamaecyparis obtusa* trees in Japan, mixed in a certain ratio may be used.

Meanwhile, when phytoncide is sprayed onto the skin, a part of the phytoncide and the like may evaporate, thus drying the skin. To address such a problem, a moisturizing agent capable of moisturizing the skin is included in the phytoncide composition.

Such a moisturizing agent preferably has a low viscosity so as not to interfere with spraying from a nozzle and to allow fine spraying of a composition including the moisturizing from the nozzle. In addition, use of the moisturizing agent is preferably minimized.

When the viscosity of the moisturizing agent is high, moisturizing effect is improved, but a particle diameter of a composition sprayed from a nozzle increases, which may cause displeasure during spraying. In addition, the composition sprayed onto the skin may run downward.

Particularly, the moisturizing agent included the composition according to the present invention is preferably gamma-poly L-glutamic acid extracted from fermented soybeans. The gamma-poly L-glutamic acid penetrates an outer layer of the skin to constantly maintain the concentration of hyaluronic acid by inhibiting the activity of a hyaluronic acid-degrading enzyme in the skin tissue, thereby making the skin healthy and inhibiting inflammation and necrosis of skin tissue.

Such gamma-poly L-glutamic acid exhibits superior moisturizing ability to hyaluronic acid conventionally used as a moisturizing agent, is eco-friendly, has little side effects, and may maintain moisturizing ability with only a small amount.

In addition, the emulsifier facilitates mixing of the undiluted phytoncide solution, as an oil ingredient, with water and the like. The emulsifier may be any one known in the art. Preferably, the emulsifier is lecithin or the like. More preferably, the lecithin is an eco-friendly substance extracted from soybeans or the like.

In another aspect, the present invention relates to a skin care spray device for hydrogen generation containing a phytoncide moisturizing liquid composition. Hereinafter, the skin care spray device for hydrogen generation containing the phytoncide moisturizing liquid composition according to the present invention is described with reference to the accompanying drawings.

FIG. 1 illustrates an internal assembly diagram of a skin care spray device for hydrogen generation containing a phytoncide moisturizing liquid composition according to the present invention; FIG. 2 illustrates sectional views of a hydrogen-generating ceramic filter; FIG. 3 illustrates a perspective view of a hydrogen-generating ceramic filter; FIG. 4 illustrates a perspective view of an aluminum pouch; FIG. 5 illustrates an upper end of an aluminum pouch and an upper end of a can coupled thereto; FIG. 6 illustrates a perspective view of a nozzle; and FIG. 7 illustrates a perspective view of a skin care spray device for hydrogen generation.

More particularly, the skin care spray device for hydrogen generation containing the phytoncide moisturizing liquid composition according to the present invention includes a hydrogen-generating ceramic filter 110 including a porous ceramic container 112, one opened end of which is sealed with a ceramic cap 113, so as to prevent external leakage of the magnesium fragments 111; an aluminum pouch 100 containing the hydrogen-generating ceramic filter 110 and a phytoncide moisturizing liquid composition 120 and provided with a check valve 140 for preventing the phytoncide moisturizing liquid composition 120 from running back from an upper part of the aluminum pouch 100; a cylindrical aluminum can 200, an open upper part of which is coupled with an upper part 150 of the aluminum pouch 100; a nozzle 300 for spraying the phytoncide moisturizing liquid composition 120 filled in the aluminum pouch 100, the nozzle 300 being mounted on an upper part of the aluminum can 200; and the like.

Here, high-purity magnesium and water should be reacted such that hydrogen is easily generated. Accordingly, to maximize the surface area of the high-purity magnesium, small magnesium fragments, as in the present invention, and the like are preferred.

Such a skin care spray device for hydrogen generation includes the aluminum pouch 100 inside which the hydrogen-generating ceramic filter 110 containing the magnesium fragments 111 is included. When the hydrogen-generating ceramic filter 110 contacts the phytoncide moisturizing liquid composition 120 as a mixture of water, an undiluted phytoncide solution, gamma-poly L-glutamic acid, chitosan, an emulsifier, and the like, magnesium reacts with water to generate hydrogen as represented by Formula 1 below. The aluminum pouch 100 is filled with the generated hydrogen:

$$Mg+2H_2O \rightarrow Mg(OH)_2+H_2 \quad \text{(Formula 1)}$$

In an embodiment, the content of hydrogen completely saturated in the aluminum pouch 100 having a volume of about 100 ml is about 1000 ppb. The content of hydrogen in the aluminum pouch 100 is preferably about 750 to 1000 ppb, more preferably about 876 ppb.

Meanwhile, the aluminum pouch 100 may prevent hydrogen present in the aluminum pouch 100 from leaking to the outside, unlike a conventional technology, due to a dense outer structure of the aluminum pouch 100. Accordingly, the efficiency of hydrogen use increases, whereby the phytoncide moisturizing liquid composition 120 in which hydrogen is rich may be sprayed through the nozzle 300.

In addition, an interior of the aluminum can 200 is sealed due to coupling between an upper part of the open cylindrical aluminum can 200, which is open, and the upper end 150 of the aluminum pouch 100. Preferably, the aluminum can 200 further includes the air 400 having a predetermined pressure therein. Here, the pressure of the air 400 is more preferably about 6 to 9 bar, most preferably about 8 bar.

When the pressure of the air 400 inside the aluminum can 200 is less than about 6 bar, pressure pressing the aluminum pouch 100 is excessively decreased, whereby spraying effect of hydrogen and the phytoncide moisturizing liquid composition 120 may be decreased. On the other hand, when the pressure of the air 400 is greater than about 9 bar, an interior pressure of the aluminum can 200 excessively increases, whereby the hydrogen and the phytoncide moisturizing liquid composition 120 in the aluminum pouch 100 may escape.

Here, the phytoncide moisturizing liquid composition 120 preferably includes water, an undiluted phytoncide solution extracted from the *chamaecyparis obtusa* tree, gamma-poly L-glutamic acid, chitosan, an emulsifier, and the like. More particularly, the water is included in an amount of about 95 to 98% by weight, the undiluted phytoncide solution is included in an amount of about 1 to 3% by weight, the gamma-poly L-glutamic acid is included in an amount of about 0.05 to 0.5% by weight, the chitosan is included in an amount of about 0.05 to 0.5% by weight, and the emulsifier is included in an amount of about 0.1 to 2% by weight, based on a total weight of the phytoncide moisturizing liquid composition.

Here, the phytoncide moisturizing liquid composition 120 preferably, further includes 0.1 to 2% by weight of a botanical extract and the like. The botanical extract is preferably an aloe extract, a citrus oil, or the like.

Particularly, when the volume of the aluminum pouch 100 is, for example, about 100 ml, the amount of the water is most preferably about 97 ml, the amount of the undiluted phytoncide solution is most preferably about 2 ml, the amount of the gamma-poly L-glutamic acid is most preferably about 0.1 ml, the amount of the chitosan is most preferably about 0.1 ml, and the amount of the emulsifier is most preferably about 0.15 ml. Here, the volume of the aluminum pouch may be increased or decreased as needed. Depending upon the increased or decreased aluminum pouch volume, the amount of the phytoncide moisturizing liquid composition 120 contained in the aluminum pouch may be changed.

In another aspect, the present invention relates to a method of manufacturing the skin care spray device for hydrogen generation, the method including a step of previously installing a hydrogen-generating ceramic filter inside an aluminum pouch and a step of injecting the phytoncide moisturizing liquid composition into the aluminum pouch, whereby hydrogen may be generated and the phytoncide moisturizing liquid composition is contained in the aluminum pouch.

More particularly, the method of manufacturing the skin care spray device for hydrogen generation containing the phytoncide moisturizing liquid composition 120 according to the present invention includes a step of manufacturing the hydrogen-generating ceramic filter 110 by inserting the magnesium fragments 111 into the porous ceramic container 112 that has been plasticized, and sealing the ceramic cap 113; a step of cutting a lower part of the prepared aluminum pouch 100 and then inserting the manufactured hydrogen-generating ceramic filter 110 into the aluminum pouch 100, followed by sealing the cut portion of the aluminum pouch 100; a step of coupling the upper part 150 of the aluminum pouch 100 including the hydrogen-generating ceramic filter 110 therein with an upper part of the cylindrical aluminum can 200 and sealing the aluminum can 200 such that the air 400 in the aluminum can 200 does not escape to the outside; a step of mixing water, an undiluted phytoncide solution extracted from a *chamaecyparis obtusa* tree, gamma-poly L-glutamic acid, chitosan, an emulsifier, and the like by means of a homomixer at about 15 to 25° C. for about 1 to 3 hours, and then preparing the phytoncide moisturizing liquid composition 120 having an average particle diameter of greater than 0 nm and 20 nm or less by means of a high-pressure nano homogenizer; a step of filling the aluminum pouch 100 and the like with the prepared phytoncide moisturizing liquid composition 120 by forcibly injecting the prepared phytoncide moisturizing liquid composition 120 into the aluminum pouch 100 via the hole 130 that includes the nozzle 300, which is located at an upper end of the aluminum can 200, mounted thereon and passes through the upper part 150 of the aluminum pouch 100; a step of mounting the nozzle 300 on an upper part of the aluminum can 200 so as to spray the phytoncide moisturizing liquid composition 120 filling the aluminum pouch 100 into the atmosphere; and the like.

More particularly, when an upper part of the open cylindrical aluminum can 200 is coupled with the upper part 150 of the aluminum pouch 100 such that the interior of the aluminum can 200 is sealed, the aluminum can 200 preferably, further includes the air 400 having a predetermined pressure therein. Here, the pressure of the air 400 is more preferably about 6 to 9 bar, most preferably about 8 bar.

Meanwhile, when the phytoncide moisturizing liquid composition 120 according to the present invention is injected into the aluminum pouch 100 in the cylindrical aluminum can 200, the volume of the aluminum pouch 100 increases and, at the same time, the pressure of the air 400 in the aluminum can 200 further increases.

Accordingly, when the nozzle 300 at an upper part of the aluminum can 200 is pushed and operated in a state in which the pressure of the air 400 in the aluminum can 200 is increased due to injection of the phytoncide moisturizing liquid composition 120, the phytoncide moisturizing liquid composition 120, which is saturated with hydrogen, in the aluminum pouch 100 is more easily sprayed to the outside.

Here, when the pressure of the air 400 in the aluminum can 200 is less than about 6 bar, a pushing pressure applied to the aluminum pouch 100 is excessively low, whereby spraying effect of hydrogen and the phytoncide moisturizing liquid composition 120 may be decreased. On the other hand, when the pressure of the air 400 is greater than about 9 bar, the hydrogen and the phytoncide moisturizing liquid composition 120 in the aluminum pouch 100 may leak out due to a high internal pressure of the aluminum can 200.

Here, the phytoncide moisturizing liquid composition 120 preferably includes water, an undiluted phytoncide solution extracted from a *chamaecyparis obtusa* tree, gamma-poly L-glutamic acid, chitosan, an emulsifier, and the like as essential ingredients. More preferably, the emulsifier includes lecithin and the like. The emulsifier may selectively, further include a botanical extract and the like.

More particularly, the water is preferably included in an amount of about 95 to 98% by weight, the undiluted phytoncide solution extracted from a *chamaecyparis obtusa* tree is preferably included in an amount of about 1 to 3% by weight, the gamma-poly L-glutamic acid is preferably included in an amount of about 0.05 to 0.5% by weight, the chitosan is preferably included in an amount of about 0.05 to 0.5% by weight, and the emulsifier is preferably included in an amount of about 0.1 to 2% by weight, based on a total weight of the phytoncide moisturizing liquid composition. More preferably, the water is included in an amount of about 97.65% by weight, the undiluted phytoncide solution extracted from a *chamaecyparis obtusa* tree is included in an amount of about 2% by weight, the gamma-poly L-glutamic acid is included in an amount of about 0.1% by weight, the chitosan is included in an amount of 0.1% by weight, and the emulsifier is included in an amount of about 0.15% by weight, based on a total weight of the phytoncide moisturizing liquid composition.

In particular, when the volume of the aluminum pouch 100 is, for example, about 100 ml, the volume of the water is most preferably about 97.65 ml, the volume of the undiluted phytoncide solution extracted from a *chamaecyparis obtusa* tree is most preferably about 2 ml, the volume of the gamma-poly L-glutamic acid is most preferably about 0.1 ml, the volume of the chitosan is most preferably about 0.1 ml, and the volume of the emulsifier is most preferably about 0.15 ml. Here, the volume of the aluminum pouch 100 may be increased or decreased as needed.

In addition, since high-purity magnesium should react with water for easy generation of hydrogen, the small magnesium fragments 111 described in the present invention are preferred so as to maximize a surface area of high-purity magnesium.

For example, when about 20 g of the magnesium fragments 111 reacts with water, hydrogen is generated. Due to the generated hydrogen, the aluminum pouch 100 having a volume of about 100 ml is filled with the hydrogen, and the hydrogen in the aluminum pouch 100 reaches the maximum saturation state within about 24 hours. As such, about 20 g of the magnesium fragments 111 used in the 100 ml aluminum pouch 100 may generate hydrogen over a period of three months.

DESCRIPTION OF SYMBOLS

100: ALUMINUM POUCH
110 HYDROGEN-GENERATING CERAMIC FILTER
111 111: MAGNESIUM FRAGMENTS
112: POROUS CERAMIC CONTAINER
113: CERAMIC CAP
120: PHYTONCIDE MOISTURIZING LIQUID COMPOSITION
130: HOLE
140: CHECK VALVE FOR PREVENTING BACKFLOW
150: UPPER PART
200: ALUMINUM CAN
300: NOZZLE
400: AIR

The invention claimed is:

1. A skin care spray device for hydrogen generation, comprising:
   a hydrogen-generating ceramic filter comprising a porous ceramic container containing magnesium fragments, one opened end of which is sealed with a ceramic cap, so as to prevent external leakage of the magnesium fragments;
   an aluminum pouch containing the hydrogen-generating ceramic filter and a phytoncide moisturizing liquid composition and provided with a check valve for preventing the phytoncide moisturizing liquid composition from running back from an upper part of the aluminum pouch;
   a cylindrical aluminum can, an open upper part of which is coupled with the upper part of the aluminum pouch; and
   a nozzle for spraying the phytoncide moisturizing liquid composition filled in the aluminum pouch, the nozzle being mounted on an upper part of the aluminum can.

2. The skin care spray device according to claim 1, wherein the cylindrical aluminum can having been sealed comprises air having a predetermined pressure therein, wherein the pressure of the air is 6 to 9 bar.

3. The skin care spray device according to claim 1, wherein the phytoncide moisturizing liquid composition comprises 95 to 98% by weight of water, 1 to 3% by weight of an undiluted phytoncide oil, 0.05 to 0.5% by weight of gamma-poly L-glutamic acid, 0.05 to 0.5% by weight of chitosan, and 0.1 to 2% by weight of an emulsifier, based on a total weight of the phytoncide moisturizing liquid composition.

4. The skin care spray device according to claim 3, wherein the phytoncide moisturizing liquid composition further comprises 0.1 to 2% by weight of a botanical extract.

5. The skin care spray device according to claim 4, wherein the botanical extract is an aloe extract or a citrus oil.

* * * * *